(12) United States Patent
O'Keefe et al.

(10) Patent No.: US 7,883,486 B2
(45) Date of Patent: Feb. 8, 2011

(54) PROTECTIVE PAD FOR USE WITH AN ORTHOPEDIC BRACE

(76) Inventors: Deborah A. O'Keefe, 632 Autumns Way Blvd., Kalamazoo, MI (US) 49009; Susan D. Rosprim, 3037 La Mancha Ct. NW., Albuquerque, NM (US) 87104

( * ) Notice: Subject to any disclaimer, the term of this patent is extended or adjusted under 35 U.S.C. 154(b) by 113 days.

(21) Appl. No.: 11/873,470

(22) Filed: Oct. 17, 2007

(65) Prior Publication Data

US 2009/0105626 A1   Apr. 23, 2009

(51) Int. Cl.
*A61F 5/00* (2006.01)
(52) U.S. Cl. ...................................................... 602/19
(58) Field of Classification Search .................. 602/19, 602/6, 20, 16; 2/464, 455, 467, 463; 128/869, 128/876

See application file for complete search history.

(56) References Cited

U.S. PATENT DOCUMENTS

| | | | |
|---|---|---|---|
| 2,349,710 A | 5/1944 | Evans | |
| 3,053,253 A | 9/1962 | Liloia et al. | |
| 3,812,862 A | 5/1974 | Bernstein | |
| 4,193,395 A | 3/1980 | Gruber | |
| 4,377,160 A | 3/1983 | Romaine | |
| 4,539,982 A | 9/1985 | Bailly | |
| 4,788,972 A | 12/1988 | DeBusk | |
| 4,833,730 A | 5/1989 | Nelson | |
| 5,019,064 A | 5/1991 | Eilender | |
| D333,939 S | 3/1993 | Gates | |
| 5,209,722 A | 5/1993 | Miklaus et al. | |
| 5,321,252 A | 6/1994 | Pickering, Jr. et al. | |
| 5,324,252 A | 6/1994 | Libbey et al. | |
| 5,366,439 A | 11/1994 | Peters | |
| 5,425,702 A | 6/1995 | Carn et al. | |
| 5,439,439 A | 8/1995 | Green et al. | |
| 5,445,858 A | 8/1995 | Nwoko | |
| 5,503,908 A | 4/1996 | Faass | |
| 5,540,964 A | 7/1996 | Mallen | |
| 5,591,122 A | 1/1997 | Yewer, Jr. | |
| 5,674,523 A | 10/1997 | Cartmell et al. | |
| 5,695,452 A | 12/1997 | Grim et al. | |
| 5,728,147 A | 3/1998 | Thomas | |
| 5,779,658 A | 7/1998 | Saca | |
| 5,840,050 A | 11/1998 | Lerman | |
| 5,916,184 A | 6/1999 | McKeel | |
| 5,939,339 A | 8/1999 | Delmore et al. | |
| 6,024,714 A | 2/2000 | Katzin | |
| 6,071,256 A | 6/2000 | Lam | |
| 6,145,134 A * | 11/2000 | Davis et al. ..................... 2/463 |
| 6,213,968 B1 | 4/2001 | Heinz et al. | |

(Continued)

*Primary Examiner*—Michael A. Brown
(74) *Attorney, Agent, or Firm*—Price, Heneveld, Cooper, DeWitt & Litton LLP

(57) ABSTRACT

A conformable pad (100) for use under an orthopedic brace includes an upper edge (101) having a straight dimension and a lower edge (108) having an uneven dimension with at least one wide section (101) and at least one narrow section (115). The pad (100) further includes a first edge (117) having a straight dimension and positioned adjacent to the at least one wide section (101) and a second edge (119) also having a straight dimension and positioned adjacent to the at least one narrow section (115) such that the first edge (117) is longer than the second edge (119). The invention is advantageous for use with orthopedic braces in order to prevent friction and irritation created by the brace against the user's skin.

20 Claims, 3 Drawing Sheets

U.S. PATENT DOCUMENTS

| | | |
|---|---|---|
| 6,362,387 B1 | 3/2002 | Carlson et al. |
| 6,374,408 B1 | 4/2002 | Tomlinson et al. |
| 6,443,920 B1 | 9/2002 | Clement |
| 6,540,703 B1 | 4/2003 | Lerman |
| 6,676,620 B2 | 1/2004 | Schwenn et al. |
| 6,861,379 B1 | 3/2005 | Blaszczykiewicz |
| 2001/0020144 A1 | 9/2001 | Heinz et al. |

* cited by examiner

PROTECTIVE PAD FOR USE WITH AN ORTHOPEDIC BRACE

FIELD OF THE INVENTION

The present invention relates generally to protective padding worn on the body and more particularly to a protective pad worn under an orthopedic brace.

BACKGROUND

Foam padding for protecting the human body is known in the art particularly in situations to prevent frictional movement against body parts that would produce skin irritation. For example, Gates U.S. Pat. No. D333,939 illustrates a design for a back support cushion. U.S. Pat. No. 5,019,064 to Ellender teaches the use of a low-friction multilayer pad with foam backing for reducing share and friction forces on a user's body. U.S. Pat. No. 4,788,972 to DeBusk teaches the use of padding for an orthopedic support device that includes a resilient foam plastic layer and fabric layer for placement against a body member. U.S. Pat. No. 3,812,862 to Bernstein teaches a waist supporting garment having two belt members that encircle the waist of the user in the manner of a corset or girdle. U.S. Pat. No. 6,374,408 to Tomlinson et al. teaches a protective athletic pad for use across a knee or elbow to protect the user from abrasion and bruising during sports activities. Finally, U.S. Pat. No. 6,362,387 to Carlson et al. teaches a self-adhering liner that is sized to low-friction support for a portion of a human body for a shoe or prosthetic socket.

Users of these types of devices often find that these pads do not stay firmly in position nor do they work well with Thoraco-Lumbo-Sacral-Orthosis (TLSO) type of braces and the like.

BRIEF DESCRIPTION OF THE FIGURES

The accompanying figures, where like reference numerals refer to identical or functionally similar elements throughout the separate views and which together with the detailed description below are incorporated in and form part of the specification, serve to further illustrate various embodiments and to explain various principles and advantages all in accordance with the present invention.

Figure 1:
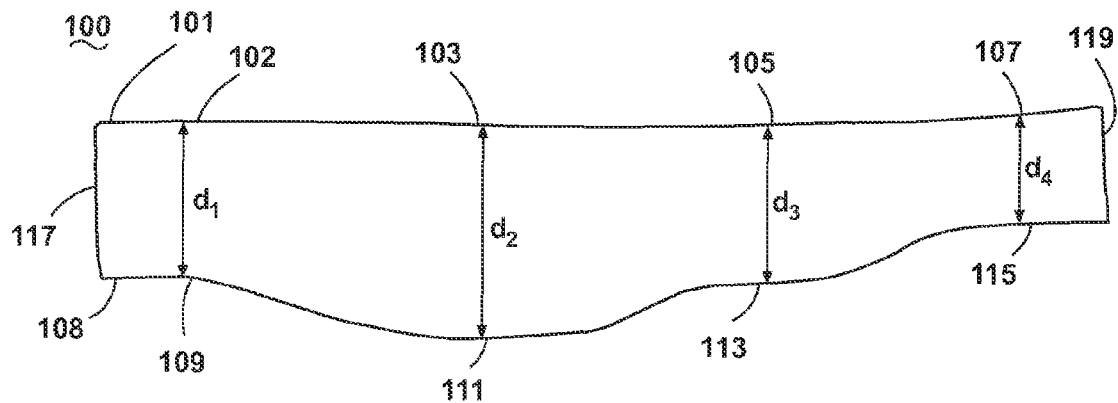
FIG. 1 is a top view of a protective pad for an orthopedic brace in accordance with some embodiments of the invention.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

DETAILED DESCRIPTION

Before describing in detail embodiments that are in accordance with the present invention, it should be observed that the embodiments reside primarily in combinations of method steps and apparatus components related to protective pad for use with an orthopedic brace. Accordingly, the apparatus components and method steps have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

In this document, relational terms such as first and second, top and bottom, and the like may be used solely to distinguish one entity or action from another entity or action without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

Figure 2:
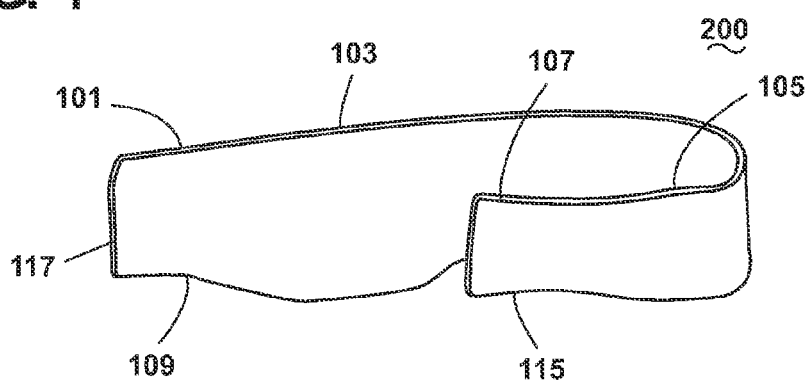
FIG. 2 is a perspective view of the pad shown in FIG. 1 positioned in a semi-circular manner.
Figure 3:
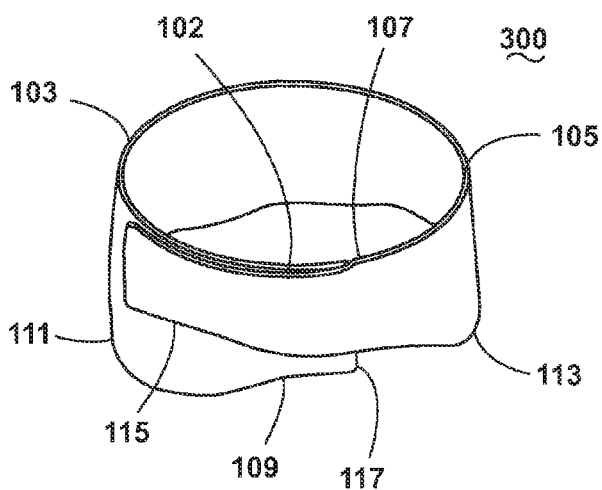
FIG. 3 is a perspective view of the pad shown in FIG. 1 positioned in a circular manner.

As seen in FIGS. 1-3, the pad 100 for use with an orthopedic brace includes a long upper edge 101, having a plurality of upper edges 102, 103, 105, 107. The total length of the upper edge might typically be 135 centimeters (cm) or similar in order to accommodate a wide range of persons using the pad. A non-linear lower edge 108 extends long the lower portion of the pad 100 and includes a plurality of lower edges 109, 111, 113, 115. The brace 100 is further bordered by end 117 and end 119 both have a straight dimension where the side 117 is longer than side 119. In practice, the side 117 might be approximately 20 cm in length, while side 119 might be approximately 12 cm in length.

As best seen in FIG. 1, the edge 109 is located in a slightly indented section along the bottom edge 108, while edge 111 forms a first protuberance section. The first protuberance section forms a wide section or bulge in the pad 100 having the greatest width. The distance $d_1$ formed between edge 101 and edge 109 is less than the distance $d_2$ formed between edge 103 and edge 111. Distance $d_1$ might be approximately 20 cm in width, while distance $d_2$ may be approximately 28 cm in width. Similarly, the lower edge 108 then steps inwardly a predetermined distance from the edge 111 to form an edge 113. The distance $d_3$ is formed between edge 105 and edge 113 and creates a second protuberance that is narrower in width than the first protuberance. The distance $d_3$ may be approximately 20 cm in width. Finally, from the edge 113, the lower edge again steps inwardly a predetermined distance to an edge 115. The distance $d_4$ is formed between edge 107 and edge 115 and may be approximately 13 cm in width.

As specifically seen in FIGS. 2 and 3, one side of pad 200 has a foam-like texture positioned toward the user's body while having a smoother, non-textured feel on its opposite side. This type of material is like that described in U.S. Pat. No. 7,261,933 issued to Gorowicz et al., which is herein incorporated by reference. The foam-like material is commonly referred to as "energy absorbing foam," while the opposite side maybe manufactured from a 100% nylon material. The material was selected due to its ability in maintaining its uniformity and for providing resiliency with no apparent change in the configuration of the invention. Hence, the invention creates protection around the body and helps in preventing additional medical complications, such as pressure ulcers. The invention utilizes no fasteners, zippers, buttons, or any mechanical attachments for affixing the fabric around the person. As will be appreciated by those skilled in the art, this creates the unique ability for creating custom sizing for each individual. This invention was developed in order ensure there was a smooth surface between the underclothing and brace that works to prevent bunching, rolling, slipping, and/or shifting of material. The movement creates stress on the user as the user moves throughout the day as well as movement during sleep periods.

In use, as the pad 100 is wrapped around a user's body, the end having the larger edge 111 typically wrapped to approximately the middle of the body. The pad 100 encircles the body forming a circular wrap until the end having smaller edge 115 overlaps to either the left side of the user's body or the right side of the user's body. This provides an additional overlapping layer where the mechanics of the brace can frictionally wear greatly against the hip and/or leg. This ultimately protects the user from further medical complications by adding comfort during either movement and rest periods. Still yet an additional advantage of the design is the material which is very light weight and convenient to clean for personal hygienic purposes.

In use, the side having the smoother, non-textured appearance is placed against the orthopedic brace. The pad 200 is bent, folded, and/or positioned into a semi-circular shape when orienting the pad about the user's torso such that the first protuberance section located between edges 102, 111 is positioned over the user's abdomen. The first protuberance section is approximately 80 cm in length, while the second protuberance section may be approximately 30 cm in length. As seen in FIG. 3, when positioned on the user's body, the pad 300 is formed into a circular shape such that one end of the resilient material holds itself in a fixed position. This will allow end 117 to be positioned over and on top of edge 119 such that the smoother side of the pad 300 goes over the foam-like side allowing the materials to frictionally engage to hold the pad 300 around the user. In use, the pad may be rotated so that the end 117 and end 119 are positioned to be on either side of the user's torso.

Figure 4:
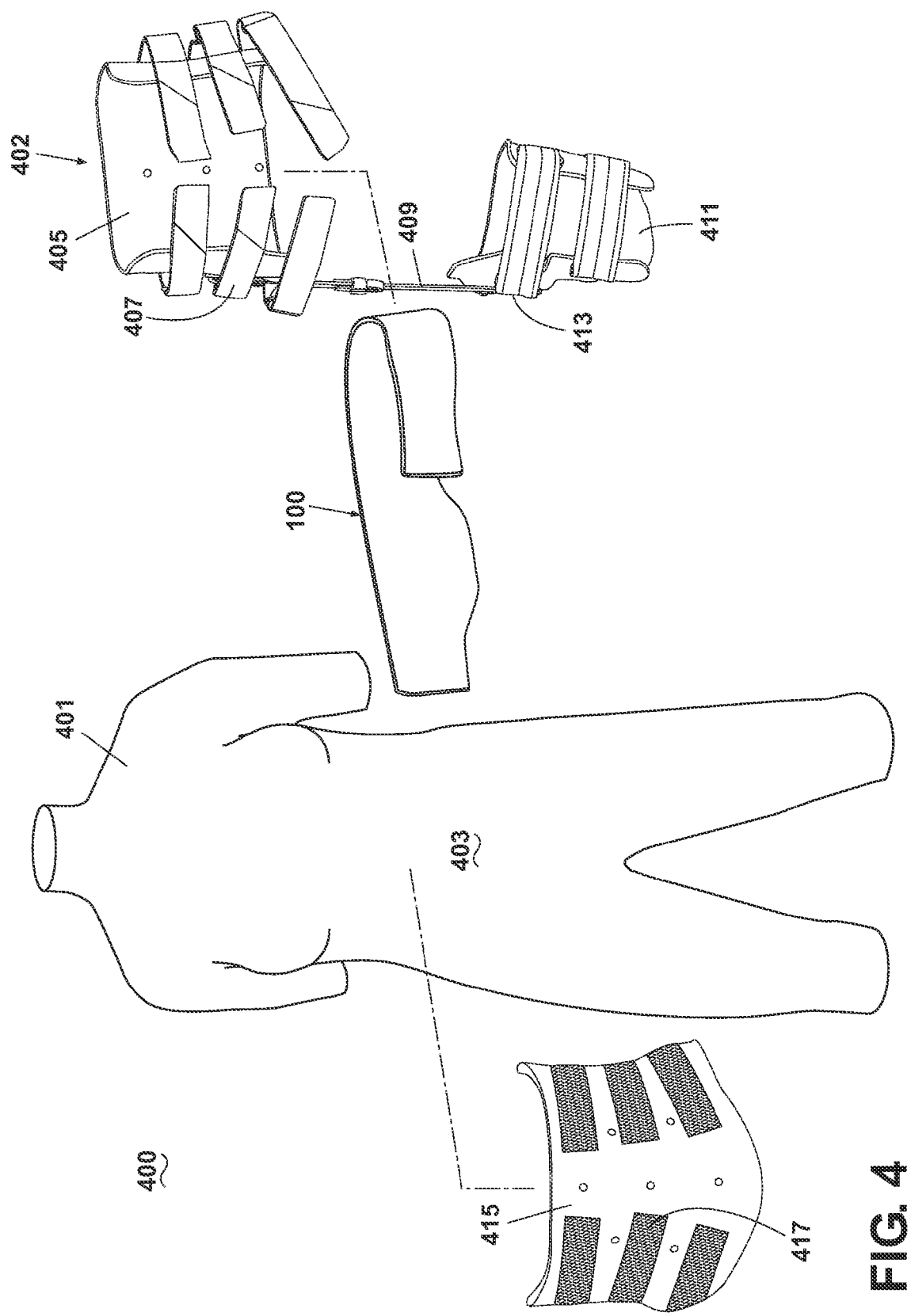
FIG. 4 is an exploded view of the pad used in connection with the orthopedic brace.
Figure 5:
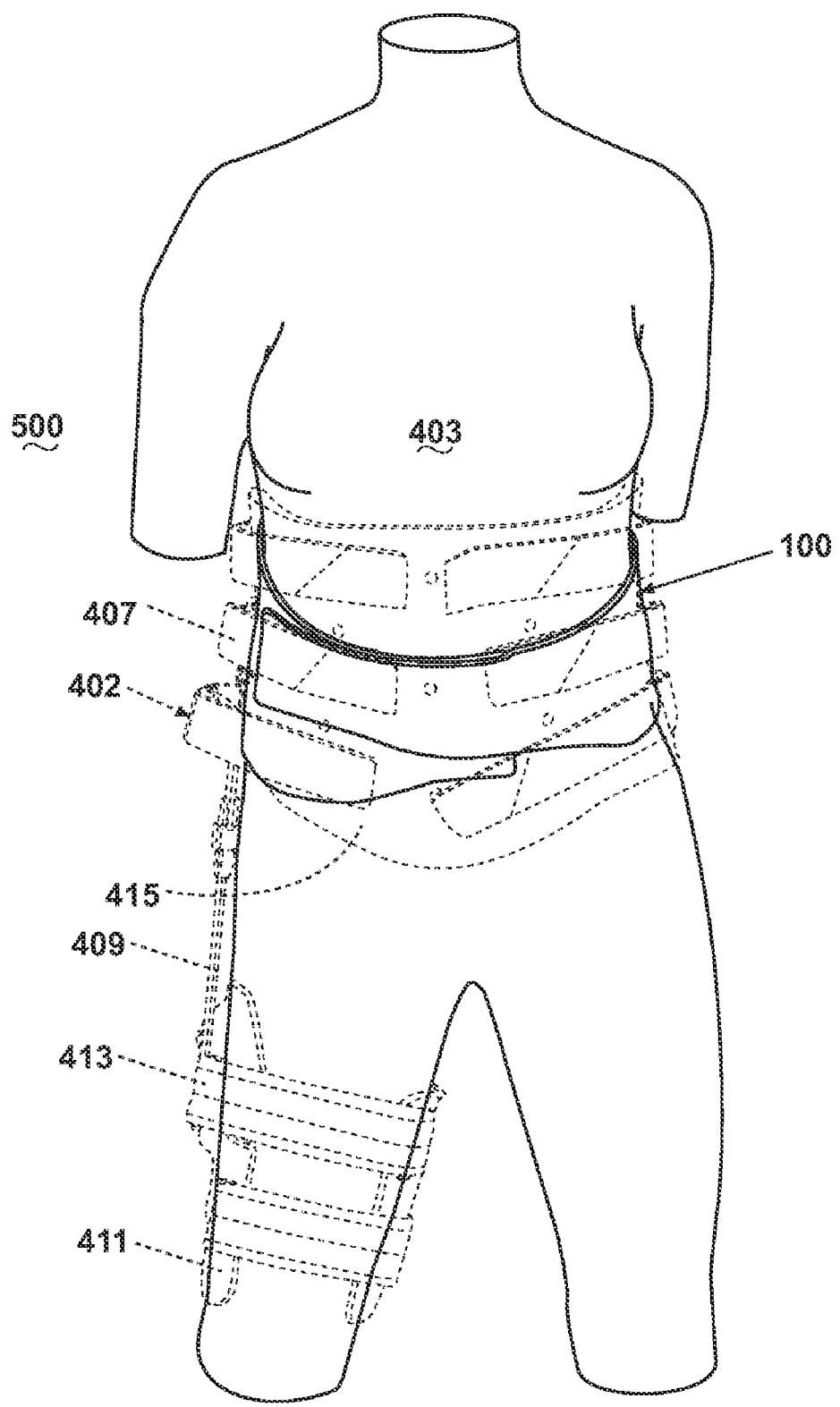
FIG. 5 is a perspective view of the pad as used in position under the orthopedic brace.

With regard to FIGS. 4 and 5, FIG. 4 is an exploded view of a pad used in connection with the orthopedic brace, such as a TLSO brace 402, while FIG. 5 is a perspective view of the pad 100 as used in position under the orthopedic brace. The pad 100 is generally placed toward the user's torso 403 in a manner like that shown in FIG. 4. While although not easily seen in FIG. 5, the user is generally clad with some type of undergarment or shirt placed over his/her torso 403. The pad 100 is wrapped around the user such that the resilient nature of the material allows the pad to frictionally engage with itself holding it into position around the torso 403. The TLSO brace 402 is then positioned over the pad 100, which provides a great amount of user comfort for preventing friction between the brace and clothing which will rub against the user's pelvis and lower lumbar regions.

As is known in the art, the TLSO brace 402 includes a rigid back section 405 and a plurality of mechanical fasteners, such as hook-and-loop fasteners 407 or the like, that are used to hold the back section 405 into a fixed position. A rigid front section 415 is generally positioned over the user's abdomen. The rigid front section 415 joins with the rigid back section 405 to prevent the user from bending or moving his/her spine from a fixed position. Further, a fastening strap 409 is connected to the back section 405 and a thigh brace 411. The thigh brace 411 is held around the user's thigh using a fastening device 413, such as a hook-and-loop fastener or the like. The thigh brace 411 and fastening strap 409 is used to hold the back section 405 into a fix position so that it does not rotate or slide upwardly on the user's torso 403.

Thus, the present invention is a low-friction pad for use with TLSO orthopedic braces and the like. The pad is configured into a unique shape so that when wrapped around the user's torso to reduce shear forces, friction, pressure, and chafing caused by the brace's movement across the user's body.

In the foregoing specification, specific embodiments of the present invention have been described. However, one of ordinary skill in the art appreciates that various modifications and changes can be made without departing from the scope of the present invention as set forth in the claims below. Accordingly, the specification and figures are to be regarded in an illustrative rather than a restrictive sense, and all such modifications are intended to be included within the scope of present invention. The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

I claim:

1. A low friction resilient foam pad that frictionally holds upon itself for use under a substantially rigid orthopedic brace comprising:
   a first straight side edge configured as a first end of the pad;
   a second straight side edge narrower in width than the first straight side edge and configured as a second end of the pad;
   a top edge having a substantially straight dimension and configured to be oriented as the top of the pad;
   a bottom edge having an uneven dimension and configured to be oriented as a bottom of the pad such that between the top edge and bottom edge is a first width positioned adjacent to the first end of the pad, a second width is positioned inwardly from the first width so the second width is wider in dimension than the first width, a third width positioned adjacent to the second width that is substantially the same dimension as the first width, and a fourth width that is narrower in dimension then the first width and is positioned adjacent to the second end of the pad; and
   wherein one side of the pad is a textured foam that faces the user's body and the opposite side of the pad is a non-textured nylon that faces outwardly from the user's body such that when the pad is wrapped around the user, the foam material engages with itself when expanded for holding the textured foam and non-textured nylon into a substantially fixed position when wrapped around the user.

2. A pad for use with an orthopedic brace as in claim 1, wherein the second width is the widest section of the pad.

3. A pad for use with an orthopedic brace as in claim 1, wherein the first width is approximately 20 cm.

4. A pad for use with an orthopedic brace as in claim 1, wherein the second width is approximately 28 cm.

5. A pad for use with an orthopedic brace as in claim 1, wherein the third width is approximately 20 cm.

6. A pad for use with an orthopedic brace as in claim 1, wherein the fourth width is approximately 13 cm.

7. A pad for use with an orthopedic brace as in claim 1, wherein the first end is approximately 20 cm.

8. A pad for use with an orthopedic brace as in claim 1, wherein the second end is approximately 12 cm.

9. A pad for use with an orthopedic brace as in claim 1, wherein the first end and the first width are substantially the same length.

10. A conformable pad for use under an orthopedic brace comprising:
   an upper edge of the pad having a substantially straight dimension configured to be oriented as the top of the pad;
   a lower edge of the pad having an uneven dimension configured to be oriented as a bottom of the pad such that between the upper edge and lower edge is a first width positioned adjacent to a first end of the pad, a second width is positioned inwardly from the first width so the second width is wider in dimension than the first width, a third width positioned adjacent to the second width and a fourth width that is narrower in dimension then the first width and is positioned adjacent to a second end of the pad such that the first end of the pad is substantially wider in dimension than the second end of the pad; and
   wherein the first end of the pad, the first width and the third width are substantially the same dimension.

11. A conformable pad for use under an orthopedic brace as in claim 10, wherein one side of the pad is a textured foam that faces the user's body and the opposite side of the pad is a non-textured nylon that faces outwardly from the user's body such that when the pad is wrapped around the user, the foam material engages with itself when expanded for holding the textured foam and non-textured nylon into a substantially fixed position without fasteners when wrapped around the user.

12. A conformable pad for use under an orthopedic brace as in claim 10, wherein the second width is the widest section of the pad.

13. A conformable pad for use under an orthopedic brace as in claim 10, wherein the fourth width is the narrowest section of the pad.

14. A conformable pad for use under an orthopedic brace comprising:
   an upper edge of the pad having a substantially straight dimension configured to be oriented as the top of the pad;
   a lower edge of the pad having an uneven dimension configured to be oriented as a bottom of the pad such that between the upper edge and lower edge is a first width positioned adjacent to a first end of the pad, a second width is positioned inwardly from the first width so the second width is wider in dimension than the first width and is configured as the widest section of the pad, a third width positioned adjacent to the second width and having substantially the same dimension as the first width, and a fourth width that is the narrowest dimension of the pad and is positioned adjacent to a second end of the pad such that the first end of the pad is substantially narrower in dimension than the second end of the pad; and
   wherein the first width and the third width are substantially the same size.

15. A conformable pad for use under an orthopedic brace as in claim 14, wherein one side of the pad is a textured foam that faces the user's body and the opposite side of the pad is a non-textured nylon that faces outwardly from the user's body such that when the pad is wrapped around the user, the foam material engages with itself when expanded for holding the textured foam and non-textured nylon into a substantially fixed position without fasteners when wrapped around the user.

16. A conformable pad for use with an orthopedic brace as in claim 14, wherein the first width and third width are approximately 20 cm.

17. A conformable pad for use with an orthopedic brace as in claim 14, wherein the second width is approximately 28 cm.

18. A conformable pad for use with an orthopedic brace as in claim 14, wherein the fourth width is approximately 13 cm.

19. A conformable pad for use with an orthopedic brace as in claim 14, wherein the first end of the pad is approximately 20 cm.

20. A conformable pad for use with an orthopedic brace as in claim 14, wherein the second end of the pad is approximately 12 cm.

* * * * *